US00RE43038E

(19) United States
(12) Reissued Patent
Osada et al.

(10) Patent Number: US RE43,038 E
(45) Date of Reissued Patent: Dec. 20, 2011

(54) COMPOUND HAVING ANTITUMOR ACTIVITY AND PROCESS FOR PRODUCING THE SAME

(75) Inventors: Hiroyuki Osada, Wako (JP); Hideaki Kakeya, Wako (JP); Yujiro Hayashi, Tokyo (JP)

(73) Assignee: Riken, Wako-shi, Saitama (JP)

(21) Appl. No.: 13/092,127

(22) PCT Filed: Jun. 6, 2003

(86) PCT No.: PCT/JP03/07189

§ 371 (c)(1),
(2), (4) Date: May 26, 2005

(87) PCT Pub. No.: WO03/104238

PCT Pub. Date: Dec. 18, 2003

Related U.S. Patent Documents

Reissue of:
(64) Patent No.: 7,612,213
Issued: Nov. 3, 2009
Appl. No.: 10/516,743
Filed: Jun. 6, 2003

(30) Foreign Application Priority Data

Jun. 7, 2002 (JP) ..... 2002-166868

(51) Int. Cl.
*C07D 207/00* (2006.01)
*C07D 209/32* (2006.01)
*C07D 303/38* (2006.01)
*C07D 491/02* (2006.01)

(52) U.S. Cl. ..... 548/400; 548/453; 548/512; 548/544; 549/548

(58) Field of Classification Search ..... 548/400, 548/453, 512, 544; 549/548
See application file for complete search history.

(56) References Cited

FOREIGN PATENT DOCUMENTS

JP 8-269061 A 10/1996

OTHER PUBLICATIONS

Golub et al, Oct. 15, 1999, Science, 286, 531-537.*
Hayashi and Narasaka, Chemistry Letters, 1998, pp. 313-314.*
Hortobagyi, G., Oct. 1, 1998, N. Engl. J. Med, 339, 974-984.*
Kuramochi et al, Tetrahedron Letters, 1999, 40, p. 7371-7374.*
Kuramochi et al., Tet. Lett., vol. 40, 1999, 7371-7374, especially p. 7371.*
Hayashi et al., Chem Lett., vol. 27(4), 1998, p. 313-314, especially p. 313.*
Patani et al., Chem Rev, 1996, vol. 96 (8), especially p. 3147.*
Nagumo et al., Bioorganic and Medicinal Chemistry Letters, vol. 14, Iss. 17, 2004, pp. 4425-4429.*
Hayashi et al., Chem. Lett., vol. 27(4), 1998, p. 313-314, especially p. 313.*
Marumoto et al., "Assymmetric total synthesis of epolactaene", Yuki Gosel Kagaku Kyokaishi, 2002, vol. 58, No. 3, pp. 183-191.

* cited by examiner

*Primary Examiner* — Susannah Chung
(74) *Attorney, Agent, or Firm* — Birch, Stewart, Kolasch & Birch, LLP

(57) ABSTRACT

A compound represented by the general formula (I): (I) wherein R represents linear, branched, or cyclic alkyl or aryl; a process for producing the compound; and an antitumor agent containing the compound as an active ingredient.

(I)

8 Claims, No Drawings

COMPOUND HAVING ANTITUMOR ACTIVITY AND PROCESS FOR PRODUCING THE SAME

Matter enclosed in heavy brackets [ ] appears in the original patent but forms no part of this reissue specification; matter printed in italics indicates the additions made by reissue.

This application is the National Stage of copending International Application No. PCT/JP03/07189 filed on Jun. 6, 2003, which designated the United States and on which priority is claimed under 35 U.S.C. 120, the entire contents of which are hereby incorporated by reference, and this application claims priority of Application No. 2002-166868 filed in Japan on Jun. 7, 2002 under 35 U.S.C. 119.

TECHNICAL FIELD

The present invention relates to a novel compound having antitumor activity, a process for producing the compound, and an antitumor agent containing the compound as an active ingredient.

BACKGROUND ART

Along with surgical therapy and radiation therapy, cancer chemotherapy plays an important role in "treatments for cancer." Starting with Nitrogen Mustard-related compounds which were clinically used as antitumor agents in 1940s, various types of antitumor agents have been developed for approximately sixty years since then. However, the antitumor agents clinically used have problems including side effects and the appearance of cells with acquired resistance. The biological activity of chemical substances depends largely on their chemical structures. Accordingly, there has been a growing demand for a novel compound having antitumor activity, which is suitable for an antitumor agent.

DISCLOSURE OF THE INVENTION

The present invention was made in order to meet the above demand. Namely, an object of the present invention is to provide a novel compound having antitumor activity, a process for producing the compound, and an antitumor agent containing the compound as an active ingredient.

The inventors of the present invention have devoted themselves to the study for attaining the above object and have completed the present invention by finding out a novel compound having antitumor activity.

That is, the present invention provides a novel compound represented by the following general formula (I):

(I)

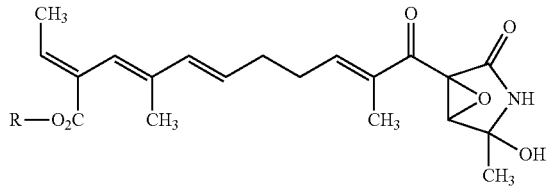

(wherein R represents a linear, branched, or cyclic alkyl or aryl group). Preferred embodiment of the present invention is a compound wherein R in the general formula (I) is a linear, branched, or cyclic alkyl group. Preferred embodiment of the present invention is a compound wherein R in the general formula (I) is a linear, branched, or cyclic alkyl group having 1 to 6 carbon atoms. Preferred embodiment of the present invention is a compound wherein R in the general formula (I) is a tert-butyl group. Preferred embodiment of the present invention is a novel compound represented by the following formula (II).

(II)

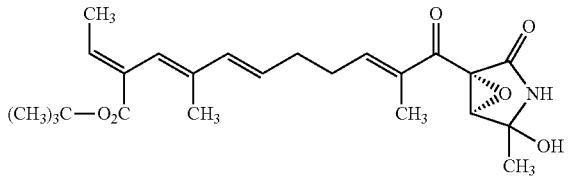

Further, the present invention provides a process for producing a compound represented by the general formula (I), comprising:

(1) reacting tetrahydropyran-2-ol with (ethoxycarbonylethylidene) triphenylphospholane;

(2) protecting a free hydroxyl group of the reaction product from (1);

(3) transforming a hydroxymethyl group of the reaction product from (2) into a formyl group;

(4) reacting the reaction product from (3) with phosphonoacetic acid ester represented by the following general formula (A):

(A)

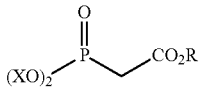

(wherein R and X each represent a linear, branched, or cyclic alkyl or aryl group);

(5) reacting the reaction product from (4) with a base and acetaldehyde;

(6) formally dehydrating the reaction product from (5);

(7) deblocking a protecting group of the reaction product from (6);

(8) oxidizing the reaction product from (7);

(9) reacting the reaction product from (8) with phosphonopropionic acid methyl ester represented by the following general formula (B):

(B)

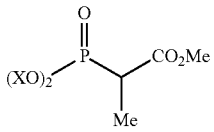

(wherein X is synonymous with the foregoing);

(10) reacting the reaction product from (9) with acetonitrile in the presence of a base;

(11) reacting the reaction product from (10) with propanal represented by the following general formula (C):

(C)

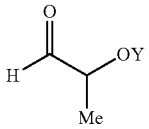

(wherein Y represents a protecting group of a hydroxyl group);

(12) epoxidizing the reaction product from (11);

(13) deblocking a protecting group of the reaction product from (12);

(14) dehydrating a cyano group from the reaction product from (13); and

(15) lactamizing the reaction product from (14).

Furthermore, the present invention provides a novel compound represented by the following general formula (III):

(III)

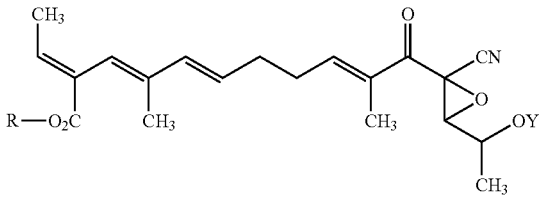

(wherein R and Y are synonymous with the foregoing).

Still further, the present invention provides a process for producing a compound represented by the general formula (III), comprising reacting a compound represented by the following general formula (IV):

(IV)

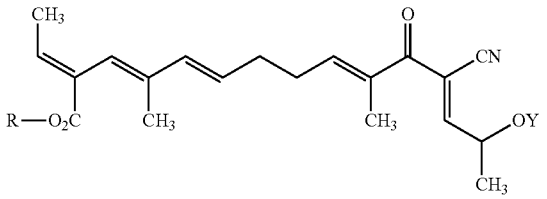

(wherein R and Y are synonymous with the foregoing) with peroxide capable of stereo selectively epoxidizing the compound.

The present invention further provides a pharmaceutical agent containing a novel compound represented by the general formula (I) as an active ingredient. Preferred embodiment of the present invention is that said pharmaceutical agent is an antitumor agent.

BEST MODE FOR CARRYING OUT THE INVENTION

Hereinafter, the present invention is described in detail.

A compound of the present invention is that represented by the following general formula (I):

(I)

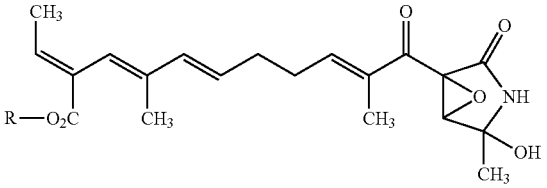

(wherein R represents a linear, branched, or cyclic alkyl or aryl group).

In the formula, R represents a linear, branched, or cyclic alkyl or aryl group, and preferably a linear, branched, or cyclic alkyl or aryl group such as a phenyl group, having 1 to 6 carbon atoms, more preferably a linear or branched alkyl group having 1 to 6 carbon atoms. More particularly, a methyl group, ethyl group, n-propyl group, isopropyl group, n-butyl group, isobutyl group, sec-butyl group, tert-butyl group, n-pentyl group, n-hexyl group, phenyl group, or the like can be used, with a tert-butyl group being preferred.

The compound of the present invention represented by the general formula (I) has several asymmetric carbons, or may additionally have one or more asymmetric carbons depending on the type of a substituent. While stereoisomers such as optical isomers and diastereoisomers based on such an asymmetric carbon exist, mixtures of any stereoisomers or racemic bodies, in addition to stereoisomers in pure form, are included in the scope of the present invention. Moreover, the compound of the present invention has an olefinic double bond. While there are geometric isomers based on a double bond, mixtures of any geometric isomers, in addition to geometric isomers in pure form, are included in the scope of the present invention. Furthermore, although the compound of the present invention may exist as a tautomer, any tautomers or mixtures thereof are included in the scope of the present invention. The compound of the present invention can take any crystal form in one form. Alternatively, the compound can exist as a hydrate or a solvate. In addition, the compound of the present invention can exist as a pharmaceutically acceptable salt in another form. Each form can be converted into a preferable form by standard manners depending on the purpose of the usage. It is obvious that any of those materials is included in the scope of the present invention.

A producing process of the present invention is a process for producing the compound represented by the general formula (I).

In the producing process of the present invention, preferably used is, but not limited to, for example a pathway indicated in Synthesis Scheme 1 described below. Acids, bases, catalysts, solvents, reaction temperatures, reaction times, and so on employed in the reaction pathway shown in Synthesis Scheme 1 can be appropriately altered based on organic synthesis approaches which are generally well known. Thus, methods including such alteration pertain to the scope of the producing process according to the present invention. In addition, the corresponding compound represented by the general formula (I) can be produced by replacing a t-butyl portion of phosphonoacetate used in the Horner-Emmons reaction of the transformation process from Compound 6 to Compound 7 in Synthesis Scheme 1, with a suitable substituent for the desired compound represented by the general formula (I).

Synthesis Scheme 1-1

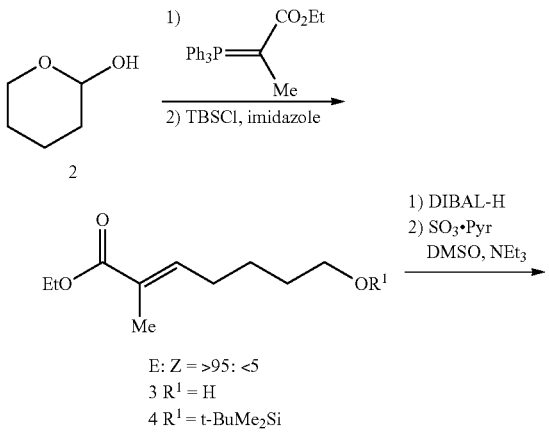

-continued
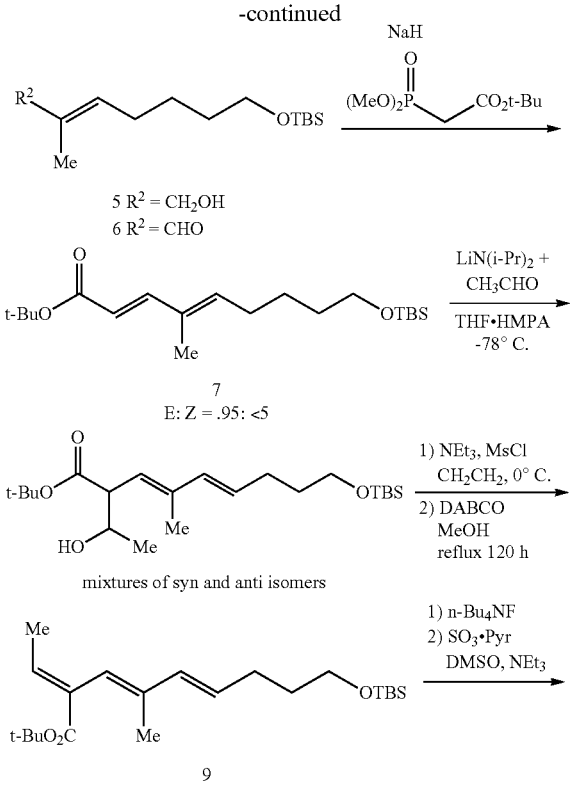
-continued
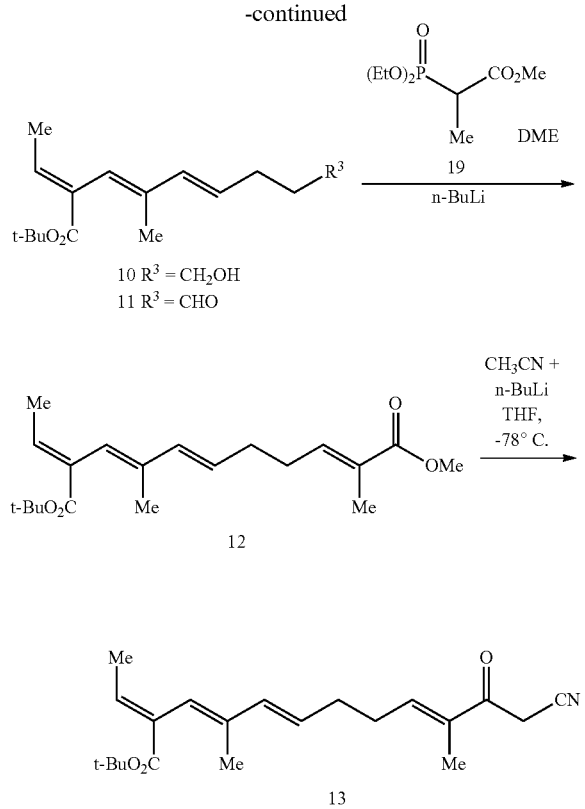
Synthesis Scheme 1-2
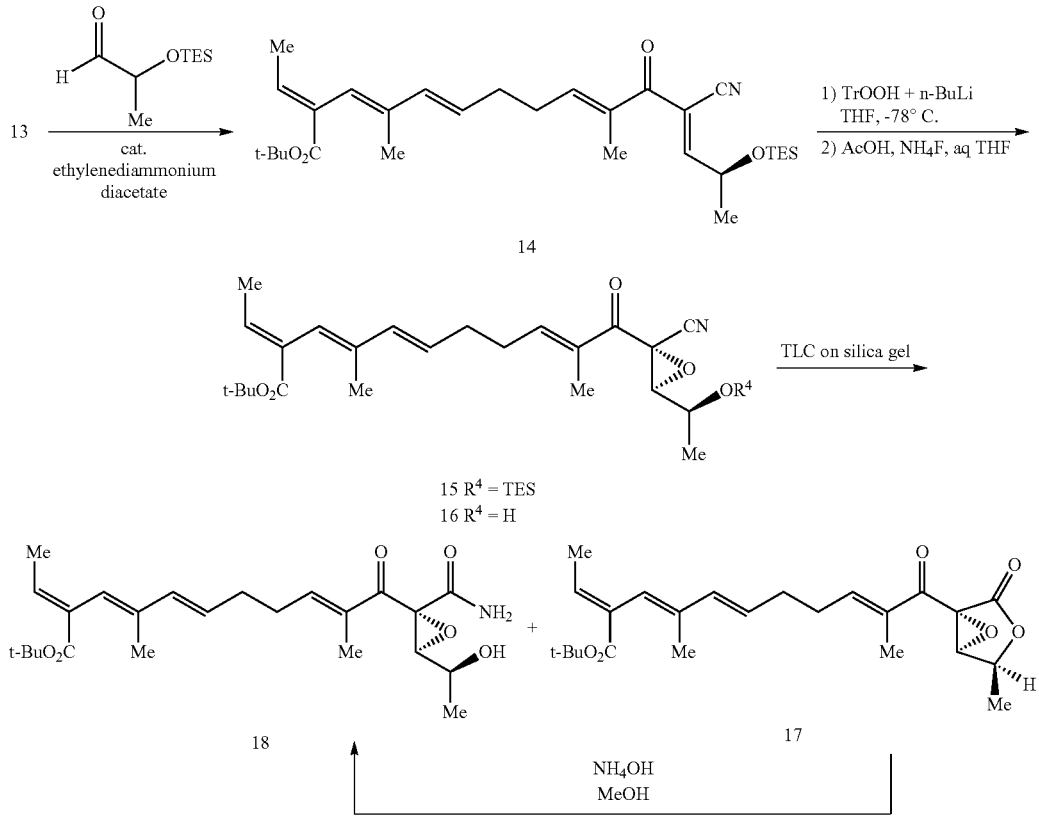

-continued

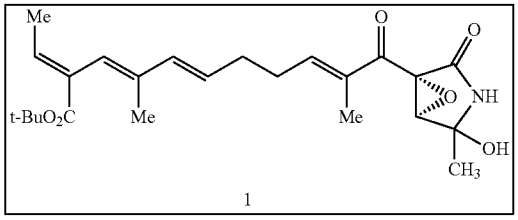

The abbreviations for Synthesis Scheme 1 is explained below.

TBSCl: tert-butyldimethylsilyl chloride
DIBAL-H: diisobutylaluminium hydride
DMSO: dimethylsulfoxide
$NET_3$: triethylamine
HMPA: hexamethylphosphoramide
MsCl: mesylchloride
DABCO: 1,4-diazabicyclo[2.2.2]octane
N-BuLi: n-butyllithium
TES: triethylsilyl
TrOOH: tritylperoxide
AcOH: acetic acid
TLC: thin-layer chromatography A variety of esters (Compound (A)) of phosphonoacetic acid used for producing Compound 7 in Synthesis Scheme 1 are represented by the following general formula (A):

(A)

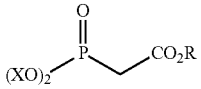

(wherein R and X each represent a linear, branched, or cyclic alkyl or aryl group).

Preferable R is described above. Further, X's each independently represent a linear, branched, or cyclic alkyl or aryl group. Preferable examples thereof include a methyl group, an ethyl group, an n-propyl group, an isopropyl group, an n-butyl group, an isobutyl group, and a phenyl group. Of those, a methyl group or an ethyl group is more preferable.

Compound (A) can be synthesized, for example, as follows.

A variety of esters of 2-bromopropionic acid (Examples of esters include linear esters, branched esters, and cyclic esters. Specific examples thereof include methyl, ethyl, n-propyl, isopropyl, n-butyl, isobutyl, sec-butyl, tert-butyl, n-pentyl, n-hexyl, and phenyl esters.) are added with equimolar amounts of trialkylphosphite or triarylphosphite (Examples of an alkyl group include a methyl group, an ethyl group, an n-propyl group, an isopropyl group, an n-butyl group, and an isobutyl group, and examples of an aryl group include a phenyl group. Of those, a methyl group or an ethyl group is preferable.). Further, in some cases, a solvent is added to the mixture, and then the whole is heated and stirred.

Although a solvent may not be utilized, if used, a halogenated hydrocarbon such as chloroform, an ether-based solvents such as THF (tetrahydrofuran), an aromatic solvent such as benzene or toluene, or the like is desirable. Heating temperature is desired to be in the range from 50° C. to 250° C. and stirring time is desired to be from 10 min to 10 hours. Purification is performed directly by distillation under reduced pressure or by silica gel chromatography or the like.

For example, a variety of esters of 2-bromopropionic acid can be obtained by stirring 2-bromopropanoyl chloride or 2-bromopropanoyl bromide with the corresponding alcohol in the presence of tertiary amine.

For example, tert-butyl diethyl phosphonoacetate of a variety of esters of phosphonoacetic acid can be obtained as follows.

Triethyl phosphite (24 cc) is added to t-butyl-2-bromopropanate (27.3 g), followed by stirring at 160° C. for 20 minutes. Distillation under reduced pressure is performed to produce tert-butyl diethyl phosphonoacetate (32 g; 91%).

Phosphonopropionic acid methyl ester (Compound (B)) used for producing Compound 12 in Synthesis Scheme 1 is represented by the following general formula (B):

(B)

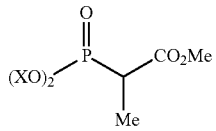

(wherein X is synonymous with the foregoing).

Preferred X is described above.

For example, diethylphosphonopropionic acid methyl ester of Compound (B) can be synthesized as follows.

24.88 g of triethyl phosphite and 25.0 g of methyl 2-bromopropionic acid are mixed and heated to reflux at 160° C. for 12 hours. 26.2 g of the object (yield: 78%) is obtained by performing distillation under reduced pressure (5 mmHg; 120° C.).

Propanal (Compound (C)) used for producing Compound 14 in Synthesis Scheme 1 is represented by the following general formula (C)

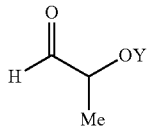

(wherein Y represents a protecting group of a hydroxyl group).

Y represents a protecting group of a hydroxyl group. Preferable examples thereof include a TBDPS (tert-butyldiphenylsilyl) group, a TBDMS (also referred to as TBS) (tert-butyldimethylsilyl) group, a TES (triethylsilyl) group, a TIPS (triisopropylsilyl) group, a DMES (dimethylethylsilyl) group, a THP (teterahydropyranyl) group, an EE (ethoxyethyl) group, a MOM (methoxymethyl) group, and a Bn (benzyl) group. Of those, a triethylsilyl group is more preferable.

Of Compounds (C), 2-(triethylsiloxy) propanal can be synthesized, for example, as follows.

Triethylsilyl chloride is added to a DMF solution of methyl lactate and imidazole and the whole is stirred at room temperature. Methyl 2-triethylsiloxy propanoate is obtained by isolation and purification using methods generally used for isolating and purifying organic compounds. Methyl 2-triethylsiloxy propanoate is reduced with isobutylaluminium hydride and 2-triethylsiloxy-1-propanol is obtained by isolation and purification using methods generally used for isolating and purifying organic compounds. 2-triethylsiloxy-1-propanol is oxidized with an oxidizing agent such as $SO_3$-pyridine in the presence of a base to produce Compound (C).

Hereinafter, each process in Synthesis Scheme 1 is described.

Compound 3 in Synthesis Scheme 1 can be obtained, for example by refluxing and reacting tetrahydropyran-2-ol and (ethoxycarbonylethylidene) triphenylphospholane for 0.1 to 10 hours. Tetrahydropyran-2-ol and (ethoxycarbonylethylidene) triphenylphospholane utilized may be commercially available (e.g., from Aldrich). Compound 3 obtained as above can be isolated and purified by using methods generally used for isolating and purifying organic compounds.

Compound 4 can be obtained by protecting a free hydroxyl group of Compound 3 with an appropriate protecting group such as a TBDPS group, TBDMS (TBS) group, TES group, TIPS group, DMES group, THP group, EE group, MOM group, or Bn group. Compound 4 obtained as above can be isolated and purified by using methods generally used for isolating and purifying organic compounds.

Compound 6 can be obtained by transforming a hydroxymethyl group of Compound 4 into a formyl group. For example, Compound 6 can be obtained as follows. Compound 5 is obtained by reducing Compound 4 with a reducing agent such as isobutylaluminium hydride, lithium aluminum hydride, or lithium borohydride. Compound 5 can be isolated and purified by using methods generally used for isolating and purifying organic compounds. Compound 5 can be subsequently oxidized with an oxidizing agent such as $SO_3$-pyridine or by Swan oxidation using oxalyl chloride or the like, preferably in the presence of a base such as triethylamine to produce Compound 6. Compound 6 obtained as above can be isolated and purified by using methods generally used for isolating and purifying organic compounds.

Compound 7 is obtained by reacting Compound 6 with a variety of esters of phosphonoacetic acid of Compound (A). For example, Compound 7 can be synthesized as follows. Preferably using a base in the reaction, an organic solvent (desirably including, but not limited to THF, diethyl ether, and DME (ethylene glycol dimethyl ether)) is added to a base such as sodium hydride (but not limited to sodium hydride, for example butyllithium or potassium hydride can be also used). To this solution, a variety of esters (as ester, linear ester, branched ester, cyclic ester, or the like, more particularly methyl, ethyl, n-propyl, isopropyl, n-butyl, isobutyl, sec-butyl, tert-butyl, n-pentyl, n-hexyl, phenyl ester, or the like) of phosphonoacetic acid are added and stirred, desirably at an addition temperature in the range of −20° C. to 60° C., desirably for a reaction time, which varies depending on the types of a base and a solvent, from 10 min to 3 hours. To this solution, Compound 6 dissolved in an organic solvent is added and stirred. Examples of an organic solvent in which Compound 6 is dissolved preferably include, but not limited to, THF, diethyl ether, and DME. The temperature for addition and stirring is desirably in the range of −20° C. to 60° C. The stirring time, which varies depending on phosphonoacetic acid utilized, is generally in the range of 10 min to 12 hours. Ester obtained as above can be isolated and purified by using methods generally used for isolating and purifying organic compounds. For example, the reaction solution is poured into a buffer solution, ammonium chloride aqueous solution, or the like and extracted with halogenated hydrocarbon such as chloroform, ether such as diethyl ether, ester such as ethyl acetate, or the like. The concentrate obtained by concentrating the extract solution is purified using silica gel column chromatography or the like.

Compound 8 can be obtained by reacting Compound 7 with acetaldehyde in the presence of a base such as lithium diisopropylamine or lithium bis(trimethylsilyl) amide. Compound 8 obtained as above can be isolated and purified by using methods generally used for isolating and purifying organic compounds.

Compound 9 can be obtained by formally dehydrating Compound 8. It is noted that "formal dehydration" in the present invention means that a double bond is formed by an elimination reaction of a hydroxyl group and a hydrogen atom. In the present invention, "formal dehydration" includes the formation of a double bond by an elimination reaction of a hydroxyl group modified (e.g., esterified) and a hydrogen atom. For example, Compound 9 can be synthesized as follows. Preferably in the presence of a base such as triethylamine and a catalyst such as DMAP, an elimination reaction proceeds concurrently with the esterification of a free hydroxyl group by reacting Compound 8 with, for example, a sulfonylating agent such as sulfonyl chloride or sulfonic anhydride to produce an E- or Z-olefin derivative. The isomerization reaction of olefin subsequently proceeds by affecting a base such as DABCO or DBU (1,8-diazabicyclo [5.4.0]undec-7-en) and Compound 9 having a desired steric structure can be obtained. Compound 9 obtained as above can be isolated and purified by using methods generally used for isolating and purifying organic compounds.

Compound 10 can be obtained by deblocking a protecting group of a hydroxyl group of Compound 9 such as a tert-butyldimethylsilyl group. Compound 10 obtained as above can be isolated and purified by using methods generally used for isolating and purifying organic compounds.

Compound 11 can be obtained by oxidizing Compound 10 with an oxidizing agent such as $SO_3$-pyridine or by Swan oxidation using oxalyl chloride or the like, preferably in the presence of a base such as triethylamine.

Compound 12 can be obtained by reacting Compound 11 with phosphonopropionic acid methyl ester of Compound (B), preferably in the presence of a base such as butyllithium. Compound 12 obtained as above can be isolated and purified by using methods generally used for isolating and purifying organic compounds.

Compound 13 can be obtained by reacting Compound 12 with acetonitrile in the presence of a base such as butyllithium or methyllithium. Compound 13 obtained as above can be isolated and purified by using methods generally used for isolating and purifying organic compounds.

Compound 14 can be obtained by reacting Compound 13 with propanal of Compound (C), preferably in the presence of an ammonium salt catalyst such as ethylenediammonium diacetate or pyridinium-p-toluenesulfonate. Compound 14 obtained as above is unstable under an acidic condition and can be quickly purified by column chromatography using florisil, or the like.

Compound 15 can be obtained by epoxidizing Compound 14. For example, Compound 15 can be synthesized as follows. Compound 15 can be obtained by reacting Compound 14 with peroxide such as tritylperoxide or t-butyl peroxide, preferably in the presence of a base such as butyllithium.

Compound 15 obtained as above can be isolated and purified by using methods generally used for isolating and purifying organic compounds. In this process, using peroxide capable of stereoselectively epoxidizing Compound 14, the compound represented by the general formula (I) can be stereoselectively synthesized. "Peroxide capable of stereoselectively epoxidizing" Compound 14 refers to sterically bulky peroxide, and specific examples thereof include tritylperoxide and t-butyl peroxide. Alternatively, using an optically active substance of Compound (C) in the prestep of this process, an optically active substance of the compound represented by the general formula (I) can be selectively synthesized.

Compound 16 can be obtained by deblocking a protecting group of a hydroxyl group of Compound 15, such as a triethylsilyl group. Compound 16 obtained as above can be isolated and purified by using methods generally used for isolating and purifying organic compounds.

Compound 18 can be obtained by hydrolyzing a cyano group of Compound 16. For example, Compound 18 can be synthesized as follows. Compounds 17 and 18 can be obtained by developing and purifying in thin-layer chromatography using, as a developing solution, an organic solvent such as ethyl acetate or hexane. Alternatively, Compounds 17 and 18 can be also obtained by affecting an acid such as acetic acid, tosylic acid, or hydrochloric acid on Compound 16. Compound 17 is transformed into Compound 18 by reacting it with ammonia water or the like. Compound 18 obtained as above can be isolated and purified by using methods generally used for isolating and purifying organic compounds.

Compound 1 can be obtained by lactamizing Compound 18. For example, Compound 1 can be synthesized as follows. A reaction with an oxidizing agent such as $SO_3$-pyridine, Dess-Martin periodinane, or pyridinium chlorochromate can be performed, preferably in the presence of a base such as triethylamine to produce Compound 1. Compound 1 obtained as above can be isolated and purified by using methods generally used for isolating and purifying organic compounds.

The compound of the present invention exhibits excellent antitumor activity as described in Test Example which is explained below. A Pharmaceutical agent of the present invention contains such a compound as an active ingredient, and preferably the pharmaceutical agent is an antitumor agent. It is noted that formulating the pharmaceutical agent of the present invention, determining a method and dosage of administration of the agent and administering the agent can be performed, based on pharmaceutical approaches which are generally well known, except that the compound of the present invention is contained as an active ingredient therein.

For administration to a human being for the purpose of treatment or prevention, the pharmaceutical agent containing the compound of the present invention as an active ingredient can be orally or parenterally administered. Examples of dosage forms include: oral agents such as powders, granules, tablets, capsules, pills, and solvents; and parenteral agents such as injections, suppositories, percutaneous absorbents, and inhalants. The effective amount of the compound can be mixed with, if necessary, a pharmaceutical additive such as an excipient, a binder, a wetting agent, a disintegrant, or a lubricant suitable for the dosage form, and the whole can be subjected to any processing to produce a pharmaceutical preparation. An injection, for example, can be formulated by mixing the compound with an appropriate carrier and sterilizing the whole. The administration dosage of the pharmaceutical agent of the present invention differs in the condition of disease, administration route, or the age or weight of a patient, and is eventually decided according to the judgment of a doctor. For example, in the case of oral administration to an adult, the administration dosage is generally 0.1-100 mg/kg per day, preferably 1-20 mg/kg per day, and in the case of parenteral administration, generally 0.01-10 mg/kg per day, preferably 0.1-2 mg/kg per day. Administration in this manner can be performed in one dose or several divided doses for a day.

If the compound of the present invention is used as a reagent, it can be dissolved in an organic solvent or a water-containing organic solvent. For example, the reagent of the present invention containing the compound of the present invention can be directly administered to various types of cultured cell lines to inhibit the growth of cancer cells. It is noted that the reagent of the present invention can be prepared and used based on biochemical approaches which are generally well known, except that the compound of the present invention is contained therein. Available organic solvents include methanol and dimethyl sulfoxide. Dosage forms include solid agents such as powders and liquid agents dissolved in organic solvents or water-containing organic solvents. The dosage of the above compound as a reagent effective for the inhibitory effect on cancer cell growth is generally 0.1-100 μg/ml at a concentration in culture medium. However, suitable dosage differs in the types of cultured cell lines and the purpose of its use and can be appropriately selected. Alternatively, the dosage other than that in the above range can be optionally used.

EXAMPLES

The present invention is described in further detail by way of the following examples, but the present invention is not limited to them.

Example 1

Hereinafter, a synthesis process for Compound 1 of the present invention using tetrahydropyran-2-ol (Compound 2) as a starting material is described. The synthesis pathway is as shown in Synthesis Scheme 1 described above.

Hereinafter, each process of Synthesis Scheme 1 is described in further detail.

Synthesis of (E)-ethyl 7-hydroxy-2-methyl-2-heptenate (3)

Tetrahydropyran-2-ol (2) (14.03 g; 0.138 mol) is added to a benzene solution (300 ml) of (ethoxycarbonylethylidene) triphenylphospholane (64.40 g; 0.178 mol) and the whole is refluxed at 90° C. for 1.5 hours. After the temperature is returned to room temperature, the solvent is then distilled off under reduced pressure, and the residue is separated and purified by column chromatography (developing solution, ethyl acetate:hexane=1:5) to produce Ester 3 (25.15 g; 0.135 mol) of 98% in yield.

$^1$H NMR ($CDCl_3$) δ=1.27 (3H, t, J=7.2 Hz), 1.48-1.61 (4H, m), 1.82 (3H, s), 1.99 (1H, bs), 2.20 (2H, q, J=7.3 Hz), 3.64 (2H, t, J=6.3 Hz), 4.17 (2H, q, J=7.2 Hz), 6.74 (1H, dt, J=1.3, 7.3 Hz); $^{13}$C NMR ($CDCl_3$) δ=12.3, 14.2, 24.7, 28.3, 32.2, 60.4, 62.4, 127.9, 141.9, 168.3; IR (neat) 3421, 2935, 1712, 1649, 1271, 1095 cm$^1$, Anal. Calcd for $C_{10}H_{18}O_3$: C, 64.49; H, 9.74%, found C, 64.39; H, 9.75%.

Synthesis of (E)-ethyl 7-(tert-butyldimethylsiloxy)-2-methyl-2-heptenate (4)

To a methylene chloride solution (300 ml) of Ester 3 (13.91 g; 0.0748 mol), 43 ml of DMF (dimethylformamide) and imidazole (7.6 g; 0.112 mol) are added and the whole is stirred until imidazole is fully dissolved. Tert-butyldimethylsilyl chloride (13.5 g; 0.0897 mol) is then added thereto and the whole is stirred for 20 min. After stirring, the resultant solution is quenched using a buffer solution (100 ml) and the organic compound is extracted three times with ethyl acetate, followed by the wash of the organic layer in a saturated saline solution and drying over anhydrous magnesium sulfate. After anhydrous magnesium sulfate is filtered and the solvent is distilled off under reduced pressure, the residue is separated and purified by column chromatography (developing solution, ethyl acetate:hexane=1:1) to produce Ester 4 (22.16 g; 0.0739 mol) of 99% in yield.

$^1$H NMR ($CDCl_3$) δ=0.01 (6H, s), 0.86 (9H, s), 1.26 (3H, t, J=7.1 Hz), 1.40-1.56 (4H, m), 1.79 (3H, s), 2.15 (2H, q, J=7.1 Hz), 3.58 (2H, t, J=6.0 Hz), 4.15 (2H, q, J=7.1 Hz), 6.72 (1H, dt, J=1.3, 7.5 Hz);

$^{13}$C NMR ($CDCl_3$) δ=−5.3, 12.3, 14.3, 18.3, 24.9, 25.7, 28.4, 32.4, 60.4, 62.8, 127.8, 142.1, 168.3; IR (neat) 2952, 2931, 1712, 1651, 1255, 1101, 837, 775 cm$^{-1}$; Anal. Calcd for $C_{16}H_{32}O_3Si$: C, 63.95; H, 10.73%, found C, 63.72; H, 10.48%.

Synthesis of (E)-7-(tert-butyldimethylsiloxy)-2-methylhept-2-en-1-ol (5)

To a methylene chloride solution (200 ml) of Ester 4 (15.84 g; 0.0528 mol), a 0.95 M diisobutylaluminiumhydride-hexane solution (139 ml; 0.132 mol) is added at 0° C. and the whole is stirred for 1 hour. After stirring, methanol (7 ml; 0.160 mol) and sodium sulfate decahydrate (68.0 g; 0.211 mol) are added thereto and the whole is stirred at room temperature for 30 min. Sodiumsulfatedecahydrate is filtered using Chloroform (21), and the solvent is distilled off under reduced pressure to produce Alcohol 5 (13.60 g; 0.0528 mol) of 100% in yield.

$^1$H NMR ($CDCl_3$) δ=0.02 (6H, s), 0.86 (9H, s), 1.32-1.43 (2H, m), 1.43-1.60 (2H, m), 1.63 (3H, s), 1.76 (1H, d, J=0.8 Hz), 2.01 (2H, q, J=7.3 Hz), 3.58 (2H, t, J=6.5 Hz), 3.97 (2H, s), 5.38 (1H, dt J=0.8, 7.0 Hz); $^{13}$C NMR ($CDCl_3$) δ=−5.3, 13.7, 18.4, 25.7, 26.0, 27.2, 32.3, 63.1, 68.9, 126.3, 134.8; IR (neat) 3307, 2929, 2858, 1649, 1101, 837, 775 cm$^{-1}$; HRMS (FAB$^+$) Calcd for $C_{14}H_{31}O_2Si$: (M+H$^+$), 259.2093. Found: m/z 259.2101.

Synthesis of (E)-7-(tert-butyldimethylsiloxy)-2-methylhept-2-enal (6)

After the addition of triethylamine (36.5 ml) to a methylene chloride solution (53 ml) of Alcohol 5 (13.6 g) and cooling to 0° C., a dimethylsulfoxide solution (53 ml) of $SO_3$-pyridine (25 g) is added thereto at 0° C. and the whole is stirred for 1.5 hours. After stirring, the resultant solution is quenched using a buffer solution (5 ml) and the organic compound is extracted three times with ethyl acetate, followed by the wash of the organic layer in a saturated saline solution and drying over anhydrous sodium sulfate. After anhydrous sodium sulfate is filtered and the solvent is distilled off under reduced pressure, the residue is separated and purified by column chromatography to produce Aldehyde 6 (12.8 g) of 94% in yield.

$^1$H NMR ($CDCl_3$) δ=0.02 (6H, s), 0.86 (9H, s), 1.51-1.55 (4H, m), 1.70 (3H, s), 2.35 (2H, q, J=6.6 Hz), 3.54-3.65 (2H, m), 6.46 (1H, dt, J=1.3, 7.4 Hz), 9.36 (1H, s); $^{13}$C NMR ($CDCl_3$) δ=5.3, 9.2, 18.3, 24.8, 25.9, 28.7, 32.4, 62.7, 139.5, 154.6, 195.2; IR (neat) 2952, 2929, 1691, 1644, 1255, 1101, 837, 775 cm$^{-1}$; HRMS (FAB$^+$) Calcd for $C_{14}H_{29}O_2Si$ (M+H$^+$), 257.1937. Found: m/z 257.1932.

Synthesis of (2E, 4E)-tert-butyl 9-(tert-butyldimethylsiloxy)-4-methylnona-2,4-dienate (7)

A THF solution (15 ml) of tert-butyldimethyl phosphonoacetate (1.257 g; 4.94 mmol) is added to a THF solution (5 ml) of sodium hydride (155.2 mg; 3.88 mmol) at 0° C., and the whole is stirred at room temperature for 0.5 hours. A THF solution (5 ml) of Aldehyde 6 (503.9 mg; 1.97 mmol) is then added thereto at 0° C. and the whole is stirred at room temperature for 0.5 hours. After stirring, the resultant solution is quenched using a buffer solution (15 ml) and the organic compound is extracted three times with ethyl acetate, followed by drying over anhydrous magnesium sulfate. After anhydrous magnesium sulfate is filtered and the solvent is distilled off under reduced pressure, the residue is separated and purified by thin-layer chromatography (developing solution, ethyl acetate:hexane=1:10) to produce Ester 7 (665.7 mg; 1.88 mol) of 96% in yield.

$^1$H NMR ($CDCl_3$) δ=0.02 (6H, s), 0.86 (9H, s), 1.35-1.58 (4H, m), 1.47 (9H, s), 1.72 (3H, s), 2.18 (2H, q, J=7.2 Hz), 3.58 (2H, t, J=6.0 Hz), 5.68 (1H, d, J=15.6 Hz), 5.85 (1H, t, J=7.2 Hz), 7.19 (1H, d, J=15.6 Hz); $^{13}$C NMR ($CDCl_3$) δ=5.3, 12.2, 18.3, 25.4, 25.9, 28.0, 28.2, 32.4, 62.9, 79.9, 117.4, 132.8, 141.4, 148.6, 167.0; IR (neat) 2929, 2858, 1709, 1622, 1255, 1151, 1101, 835, 775 cm$^{-1}$; HRMS Calcd for $C_{20}H_{38}O_3Si$: M, 354.2590. Found: m/z 354.2488.

Synthesis of (3E, 5E)-tert-butyl-(2R*)-9-(tert-butyldimethylsiloxy)-2-[(1S*)-1-hydroxyethyl]-4-methylnona-3,5-dienate (8)

To a THF solution (6.5 ml) of diisopropylamine (401.4 mg; 3.96 mmol), HMPA (1.6 ml) is added and then a 1.53M butyllithium-hexane solution (2.2 ml; 3.37 mmol) is added at 0° C., followed by stirring for 10 min. A THF solution (6 ml) of Ester 7 (665.7 mg; 1.88 mmol) is then added thereto at −78° C. and the whole is stirred for 1.5 hours. After stirring, acetaldehyde (2 ml; 35.8 mmol) is added there to at −78° C. and the whole is stirred for 3 hours. After stirring, the resultant solution is quenched using a buffer solution (30 ml) and the organic compound is extracted three times with ethyl acetate, followed by the wash of the organic layer in a saturated saline solution and drying over anhydrous sodium sulfate. After anhydrous sodium sulfate is filtered and the solvent is distilled off under reduced pressure, the residue is separated and purified by thin-layer chromatography (developing solution, ethyl acetate:hexane=1:30) to produce Syn-Aldol Product 8a (269.4 mg; 0.677 mol) and Anti-Aldol Product 8b (449.1 mg; 1.13 mol) of 96% in yield.

Syn-aldol 8a: $^1$H NMR ($CDCl_3$) δ=0.02 (6H, s), 0.87 (9H, s), 1.12 (3H, d, J=6.3 Hz), 1.42 (9H, s), 1.55-1.61 (2H, m), 1.77 (3H, s), 2.14 (2H, q, J=7.0 Hz), 2.80 (1H, d, J=3.0 Hz), 3.2 3 (1H, dd, J=4.8, 10.0 Hz), 3.59 (2H, t, J=6.3 Hz), 4.02-4.05 (1H, m), 5.47 (1H, d, J=10.0 Hz), 5.65 (1H, dt, J=15.6, 7.0 Hz), 6.1 (1H, d, J=15.6 Hz); $^{13}$C NMR ($CDCl_3$) δ=5.3, 13.2, 18.3, 19.9, 25.9, 28.0, 29.1, 32.5, 52.5, 62.5, 68.3, 81.4, 122.8, 129.3, 134.4, 138.5, 172.9; IR (neat) 3456, 2954, 2929, 1725, 1706, 1255, 1153, 1103, 835, 775 cm$^{-1}$; HRMS Calcd for $C_{22}H_{42}O_4Si$: M, 398.2852. Found: m/z 398.2840.

Anti-aldol 8b: $^1$H NMR ($CDCl_3$) δ=0.02 (6H, s), 0.8 (9H, s), 1.13 (3H, d, J=6.3 Hz), 1.41 (9H, s), 1.53-1.60 (2H, m), 1.78 (3H, s), 2.13 (2H, q, J=7.0 Hz), 2.69 (1H, d, J=5.2 Hz), 3.24 (1H, dd, J=7.8, 10.0 Hz), 3.59 (2H, t, J=6.3 Hz), 3.93-3.98 (1H, m), 5.26 (1H, d, J=10.0 Hz), 5.64 (1H, dt, J=15.6, 7.0 Hz), 6.05 (1H, d, 15.6 Hz); $^{13}$C NMR ($CDCl_3$) δ=5.3, 13.2, 18.3, 20.7, 25.9, 28.0, 29.1, 32.4, 53.9, 62.5, 69.2, 81.3, 123.9, 129.3, 134.4, 137.4, 172.9; IR (neat) 3446, 2954, 2931, 1730, 1709, 1255, 1155, 1101, 835, 775 cm$^{-1}$; HRMS Calcd for $C_{22}H_{42}O_4Si$: M, 398.2852. Found: m/z 398.286062.5, 69.2, 81.3, 123.9, 129.3, 134.4, 137.4, 172.9

IR (neat) 3446, 2954, 2931, 1730, 1709, 1255, 1155, 1101, 835, 775 cm$^{-1}$ HRMS Calcd for $C_{22}H_{42}O_4Si$: M, 398.2852. Found: m/z 398.2860

Synthesis of (3E, 5E)-tert-butyl-9-(tert-butyldimethylsiloxy)-2-[(E)-ethylid ene]-4-methylnona-3,5-dienate(9)

To a metylene chloride solution (15 ml) of Aldol 8 (4.03 g; 10.13 mmol), a catalytic amount of DMAP (4-(dimethylamino) pyridine) and triethylamine (4.6 ml; 33.00 mmol) are added and then a metylene chloride solution (20 ml) of sulfonyl chloride (2.30 g; 20.20 mmol) is added at 0° C., followed by stirring at room temperature for 1 hour. After stirring, the resultant solution is quenched using a buffer solution (50 ml) and the organic compound is extracted three times with ethyl acetate, followed by the wash of the organic layer in a saturated saline solution and drying over anhydrous magnesium sulfate. Anhydrous magnesium sulfate is filtered and the solvent is distilled off under reduced pressure.

DABCO (5.67 g; 50.65 mmol) is added to a methanol solution (50 ml) of the resultant mesylate and the whole is refluxed at 100° C. for 120 hours. After stirring, the resultant solution is quenched using a buffer solution (50 ml) and the organic compound is extracted three times with ethyl acetate, followed by the wash of the organic layer in a saturated saline solution and drying over anhydrous magnesium sulfate. After anhydrous magnesium sulfate is filtered and the solvent is distilled off under reduced pressure, the residue is separated and purified by thin-layer chromatography (developing solution, ethyl acetate:hexane=1:3) to produce Triene 9 (3.31 g; 8.71 mol) of 86% in yield (E:Z=15:1).

$^1$H NMR ($CDCl_3$) δ=0.03 (6H, s), 0.88 (9H, s), 1.45 (9H, s), 1.56-1.64 (2H, m), 1.60 (3H, d, J=0.7 Hz), 1.67 (3H, dd, J=1.0, 7.0 Hz), 2.16 (2H, q, J=7.0 Hz), 3.61 (2H, t, J=6.4 Hz), 5.68 (1H, dt, J=15.6, 7.0 Hz), 5.89 (1H, s), 6.18 (1H, d, J=15.6 Hz), 6.78 (1H, q, J=7.0 Hz); $^{13}$C NMR ($CDCl_3$) δ=−5.3, 14.6, 15.7, 18.3, 26.0, 28.1, 29.1, 32.5, 62.6, 80.3, 122.7129.6, 132.4, 134.5, 137.5, 137.9, 166.8; IR (neat) 2929, 2858, 1712, 1635, 1254, 1173, 1101, 837, 775 cm$^{-1}$; HRMS Calcd for $C_{22}H_{40}O_3Si$: M, 380.2747. Found: m/z 380.2727.

Synthesis of (3E, 5E)-tert-butyl [(2E)-ethylidene]-9-hydroxy-4-methylnona-3,5-dienate (10)

To Triene 9 (1.30 g; 3.41 mol), a 1M tetra-n-butylammonium fluoride-THF solution (10.0 ml; 10.0 mmol) is added at 0° C. and the whole is stirred at room temperature for 3 hours. After stirring, the resultant solution is quenched using a saturated ammonium chloride solution (30 ml) and the organic compound is extracted three times with ethyl acetate, followed by drying over anhydrous sodium sulfate. After anhydrous sodium sulfate is filtered and the solvent is distilled off under reduced pressure, the residue is separated and purified by column chromatography (developing solution, ethyl acetate:hexane=1:5) to produce Alcohol 10 (893.6 mg; 3.36 mol) of 99% in yield.

$^1$H NMR ($CDCl_3$) δ=1.45 (9H, s), 1.60 (3H, s), 1.65-1.71 (6H, m), 2.20 (2H, q, J=7.2 Hz), 3.64 (2H, t, J=6.5 Hz), 5.68 (1H, dt, J=15.5, 7.2 Hz), 5.90 (1H, s), 6.20 (1H, d, J=15.6 Hz), 6.77 (1H, q, J=7.2 Hz); $^{13}$C NMR ($CDCl_3$) δ=14.5, 15.7, 28.1, 29.1, 32.3, 62.4, 80.3, 122.9, 129.1, 132.3, 134.7, 137.4, 138.0, 166.7; IR (neat) 3440, 2978, 2933, 1709, 1633, 1367, 1254, 1171, 1134 cm$^{-1}$; HRMS Calcd for $C_{16}H_{26}O_3$: M, 266.1882. Found: m/z 266.1880.

Synthesis of (3E, 5E)-tert-butyl [(2E)-ethylidene]-4-methyl-9-formylocta-3,5-dienate (11)

After addition of triethylamine (0.60 ml; 4.30 mmol) to a metylene chloride solution (10 ml) of Alcohol 10 (379.0 mg; 1.42 mmol) and cooling to 0° C., a dimethylsulfoxide solution (6 ml) of $SO_3$-pyridine (452.1 mg; 2.84 mmol) is added thereto at 0° C. and the whole is stirred for 1.5 hours. After stirring, the resultant solution is quenched using a buffer solution (20 ml) and the organic compound is extracted three times with ethyl acetate, followed by the wash of the organic layer in a saturated saline solution and drying over anhydrous sodium sulfate. After anhydrous sodium sulfate is filtered and the solvent is distilled off under reduced pressure, the residue is separated and purified by column chromatography (developing solution, ethyl acetate:hexane=1:10) to produce Aldehyde 11 (376.5 mg; 1.42 mol) of 100% in yield.

$^1$H NMR ($CDCl_3$) δ=1.45 (9H, s), 1.59 (3H, d, J=1.0 Hz), 1.66 (3H, dd, J=1.2, 7.4 Hz), 2.45 (2H, q, J=7.4 Hz), 2.55 (2H, t, J=7.4 Hz), 5.65 (1H, dt, J=15.5, 6.5 Hz), 5.92 (1H, s), 6.21 (1H, d, J=15.5 Hz), 6.78 (1H, q, J=7.4 Hz), 9.77 (1H, t, J=1.4 Hz); $^{13}$C NMR ($CDCl_3$) δ=14.5, 15.6, 28.1, 29.2, 31.4, 80.4, 123.8, 127.4, 132.2, 135.6, 137.0, 138.0, 166.7, 188.24; IR (neat) 2979, 1724, 1699, 1633, 1279, 1255, 1173, 1134 cm$^{-1}$; HRMS Calcd for $C_{16}H_{24}O_3$: M, 264.1725. Found: m/z 264.1734.

Synthesis of (3E, 5E, 9E)-tert-butyl-[(2E)-ethylidene]-4,10-dimethyl-11-oxome thoxy-1-undeca-3,5,9-trienedioate (12)

To a DME solution (30 ml) of the Horner-Emmons reagent (Compound 19: 2-(diethoxy-phosphoryl)-propionic acid methyl ester) (3.37 g; 15.05 mmol), a 1.50 M butyllithium-hexane solution (8.0 ml; 12.0 mmol) is added at 0° C. and the whole is stirred for 10 min. A DME solution (15 ml) of Aldehyde 11 (1.59 g; 6.02 mmol) is then added thereto at room temperature and the whole is stirred for 0.5 hours. After stirring, the resultant solution is quenched using a buffer solution (30 ml) and the organic compound is extracted three times with ethyl acetate, followed by drying over anhydrous magnesium sulfate. After anhydrous magnesium sulfate is filtered and the solvent is distilled off under reduced pressure, the residue is separated and purified by thin-layer chromatography (developing solution, ethyl acetate:hexane=1:10) to produce Ester 12 (2.01 g; 6.02 mol) of 100% in yield.

$^1$H NMR ($CDCl_3$) δ=1.45 (9H, s), 1.60 (3H, d, J=0.8 Hz), 1.67 (3H, dd, J=1.1, 7.2 Hz), 1.82 (3H, s), 2.23-2.31 (4H, m), 3.71 (3H, s), 5.66 (1H, dt, J=15.56.5 Hz), 5.92 (1H, s), 6.21 (1H, d, J=15.5 Hz), 6.73-6.81 (2H, m); $^{13}$C NMR ($CDCl_3$) δ=12.5, 14.5, 15.7, 28.1, 28.7, 31.7, 51.7, 80.3, 123.3, 127.9, 128.4, 132.3, 135.0, 137.3, 138.0, 141.6, 166.6, 168.6; IR (neat) 2979, 2852, 1714, 1704, 1650, 1633, 1173, 1133 cm$^{-1}$; HRMS Calcd for $C_{20}H_{30}O_4$: M, 334.2144. Found: m/z 334.2139; Anal. Calcd for $C_{20}H_{30}O$: C, 71.82; H, 9.04%. found C, 72.00; H, 8.64%.

Synthesis of (3E, 5E, 9E)-tert-butyl-12-cyano-[(2E)-ethylidene]-4,10-dimethyl-11-oxododeca-3,5,9-trienoate (13)

To a THF solution (2 ml) of acetonitrile (0.040 ml; 0.767 mmol), a 1.52 M butyllithium-hexane solution (0.30 ml;

0.456 mmol) is added at −78° C. and the whole is stirred for 1 hour. After stirring, Ester 12 (84.5 mg; 0.253 mmol) is added thereto at −88° C. Immediately after the addition, the resultant solution is quenched using a buffer solution (15 ml) and the organic compound is extracted three times with ethylacetate, followed by drying over anhydrous sodium sulfate. After anhydrous sodium sulfate is filtered and the solvent is distilled off under reduced pressure, the residue is separated and purified by thin-layer chromatography (developing solution, ethyl acetate:hexane=1:10) to produce β-Ketonitrile 13 (72.5 mg; 0.211 mol) of 84% in yield.

$^1$H NMR ($CDCl_3$) δ=1.45 (9H, s), 1.60 (3H, d, J=0.6 Hz), 1.67 (3H, dd, J=1.0, 7.1 Hz), 1.82 (3H, d, J=0.6 Hz), 2.31 (2H, q, J=7.2 Hz), 2.41 (2H, q, J=7.2 Hz), 3.75 (2H, s), 5.64 (1H, dt, J=15.6, 6.8 Hz), 5.92 (1H, s), 6.21 (1H, d, J=15.6 Hz), 6.74 (1H, dt, J=1.0, 7.2 Hz), 6.77 (1H, q, J=7.2 Hz); $^{13}$C NMR ($CDCl_3$) δ=11.5, 14.5, 15.8, 28.1, 28.3, 29.2, 31.4, 80.43, 114.2, 123.9, 127.4, 132.1, 135.7, 136.3, 137.0, 138.2, 145.5, 166.5, 188.2; IR (neat) 2979, 2929, 2256, 1705, 1681, 1639, 1281, 1254, 1169, 1134 cm$^{-1}$; HRMS Calcd for $C_{21}H_{29}NO_3$: M, 343.2147. Found: m/z 343.2153; Anal. Calcd for $C_{21}H_{29}NO_3$: C, 73.44; H, 8.51; N, 4.08%. found C, 73.53; H, 8.79; N, 4.08%.

Synthesis of (3E, 5E, 9E, 12E)-tert-butyl-12-cyano-[(2E)-ethylidene]-4,10-dime thyl-11-oxo-14-triethylsiloxypentadeca-3,5,9,12-tetraenoate(14)

(S)-2-(triethylsiloxy) propanalammoniumsalt (1.7 mg; 0.0094 mmol) are added to a benzene solution (1 ml) of β-Ketonitrile 13 (73.4 mg; 0.214 mmol) and the whole is stirred at room temperature for 2 hours, before the solvent is distilled off under reduced pressure. After ammonium salt is removed by column chromatography (developing solution, ethyl acetate:hexane=1:3) using florisil, the crude product is used in a subsequent reaction.

Synthesis of (3E,5E,9E)-tert-butyl-11-[2-cyano-3-(1-triethylsiloxyethyl)oxi ranyl]-[(2E)-ethylidene]-4,10-dimethyl-11-oxoundeca-3,5,9-trie nate (15)

To a THF solution (5 ml) of tritylperoxide (0.591 g; 2.14 mmol), a 1.49M butyllithium-hexane solution (1.15 ml; 1.71 mmol) is added at −78° C. and the whole is stirred for 1 hour. After stirring, a THF solution (5 ml) of Olefin 14 is added thereto at −78° C. and the whole is stirred for 1 hour. The resultant solution is quenched using a buffer solution (10 ml) and the organic compound is extracted with ethyl acetate, followed by drying over anhydrous sodium sulfate. Anhydrous sodium sulfate is filtered and the solvent is distilled off under reduced pressure. The crude product is used in a subsequent reaction.

Synthesis of (3E,5E,9E)-tert-butyl-11-[2-cyano-3-(1-hydroxyethyl)oxiranyl]-[(2E)-ethylidene]-4,10-dimethyl-11-oxoundeca-3,5,9-trienate (16)

An acetonitrile solution (8 ml) of Epoxide 15, ion exchange water (1 ml), and lithium fluoroborate (0.400 g; 4.27 mmol) are added and the whole is stirred for 4 hours. After stirring, the resultant solution is quenched using a buffer solution (20 ml) and the organic compound is extracted with ethyl acetate, followed by drying over anhydrous sodium sulfate. After anhydrous sodium sulfate is filtered and the solvent is distilled off under reduced pressure, the residue is quickly subjected to coarse column chromatography (developing solution, ethyl acetate:hexane=1:5) to remove excess tritylperoxide. Immediately, the product is used in a subsequent reaction.

Synthesis of (3E,5E,9E)-tert-butyl-11-[2-carbamoyl-3-(1-hydroxyethyl)oxiran yl]-[(2E)-ethylidene]-4,10-dimethyl-11-oxopentadeca-3,5,9-trie noate (18)

Hydroxynitrile 16 is developed in thin-layer chromatography (developing solution, ethyl acetate:hexane=1:2). Ammonia water (0.25 ml) is added to a methanol solution (1 ml) of the mixture of the resultant Lactone 17 and Hydroxyamide 18 at 0° C. and the whole is stirred for 20 min. The resultant solution is quenched using a buffer solution (10 ml) and the organic compound is extracted with chloroform, followed by drying over anhydrous sodium sulfate. After anhydrous sodium sulfate is filtered and the solvent is distilled off under reduced pressure, the residue is separated and purified by thin-layer chromatography (developing solution, ethyl acetate:hexane=3:1) to produce Hydroxyamide 18 (12.7 mg; 0.0290 mmol) of 14% in yield in five steps.

$^1$H NMR ($CDCl_3$) δ=1.35 (3H, d, J=3.2 Hz), 1.45 (3H, s), 1.59 (3H, s), 1.67 (3H d, J=7.0 Hz), 1.78 (3H, s), 2.31-2.37 (2H, m), 2.37-2.48 (2H, m), 3.14 (1H, d, J=7.9 Hz), 3.68-3.75 (1H, m), 5.67 (1H, dt, J=15.5, 7.3 Hz), 5.91 (1H, s), 6.22 (1H, d, J=15.5 Hz), 6.41 (1H, s), 6.77 (1H, q, J=7.0 Hz), 7.08 (1H, t, J=6.7 Hz): $^{13}$C NMR ($CDCl_3$) δ=11.3, 14.4, 15.6, 20.3, 28.1, 28.9, 31.3, 65.5, 65.5, 66.1, 80.6, 123.4, 127.8, 132.2, 135.0, 135.8, 137.8, 138.2, 149.7, 166.8, 167.3, 192.9: IR (neat) 3419, 3323, 2979, 2931, 1709, 1668, 1633, 1597, 1435, 1254, 1169 cm$^{-1}$ Synthesis of (3E,5E,9E)-tert-butyl-2-ethylidene-11-(4-hydroxy-4-methyl-2-ox o-6-oxa-3-aza-bicyclo[3.1.0]hex-1-yl)-4,10-dimethyl-11-oxounde ca-3,5,9-trienoate (1)

After the addition of triethylamine (72 μl; 0.517 mmol) to a methylene chloride solution (0.5 ml) of Hydroxyamide 18 (11.7 mg; 0.0256 mmol) and cooling to 0° C., a dimethylsulfoxide solution (0.3 ml) of $SO_3$-pyridine (56.2 mg; 0.353 mmol) is added thereto at 0° C. and the whole is stirred for 2 hours. After stirring, the resultant solution is quenched using a buffer solution (10 ml) and the organic compound is extracted with ethyl acetate, followed by the wash of the organic layer in a saturated saline solution and drying over anhydrous sodium sulfate. After anhydrous sodium sulfate is filtered and the solvent is distilled off under reduced pressure, the residue is separated and purified by thin-layer chromatography (developing solution, ethyl acetate:hexane=3:1) to produce Compound 1 of the present invention (5.2 mg; 0.0121 mol) of 48% in yield.

$^1$H NMR ($CDCl_3$) δ=1.48 (9H, s), 1.58 (3H, s), 1.61 (6H, s), 1.72 (3H, d, J=7.3 Hz), 1.86 (3H, s), 2.28-2.39 (3H, m), 2.25-2.58 (1H, m), 3.87 (1H, d, J=2.4 Hz), 4.25 (1H, brs), 5.66 (1H, dt, J=7.3, 15.6 Hz), 5.87 (1H, s), 6.23 (1H, d, J=15.7 Hz), 6.38 (1H, s), 6.78-6.85 (2H, m): $^{13}$C NMR ($CDCl_3$) δ=11.3, 14.3, 15.6, 22.4, 27.9, 28.1, 31.2, 62.2, 64.7, 81.5, 83.7, 122.8, 128.0, 131.8, 136.0, 136.4, 139.1, 139.4, 146.8, 167.8, 169.5, 189.7: IR (neat) 3417, 2979, 2929, 1709, 1682, 1635, 1367, 1284, 1257, 1167, 1136 cm$^{-1}$: $[\alpha]_D^{26}$+23 (C=0.09, MeOH):

HRMS Calcd for $C_{24}H_{33}NO_6$: M, 431.2308. Found: m/z 431.2297.

The activity of the compound of the present invention was measured according to the following method.

Test Example

Antitumor Activity of Compound 1 of Present Invention

SH-SY5Y cells of human neuroblastoma were cultured in DMEM medium (Dulbecco's modified Eagle medium) (containing 5% fetal bovine serum). Compound 1 of the present invention in a series of dilutions was added thereto and cultured at 37° C. under a 5% carbon dioxide atmosphere for 48 hours, followed by adding a MTT (3-(4,5-dimethyl-thiazol-2-yl)-2,5-diphenyl tetrazoliumbromide) reagent and further culturing for 2 to 4 hours. Absorbance at 570 nm was then measured to calculate the survival ratio. As a result, Compound 1 of the present invention had a concentration of 0.4 μg/ml at a 50% growth-inhibiting concentration.

This result indicates that Compound 1 of the present invention is effective as an antitumor agent.

INDUSTRIAL APPLICABILITY

A novel compound of the present invention has antitumor activity, and is excellent as an antitumor agent.

The invention claimed is:

1. A compound represented by the following general formula (I)

(I)

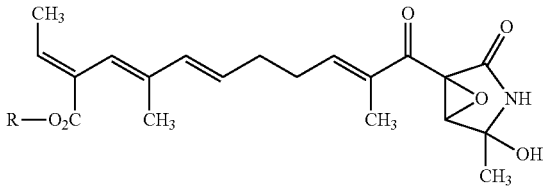

wherein R in the general formula (I) is a tert-butyl group.

2. A process for producing a compound represented by the following general formula (I):

(I)

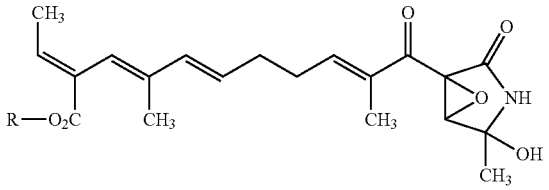

wherein R represents a linear, branched, or cyclic alkyl having 2 or more carbon atoms or an aryl group comprising:

(1) reacting tetrahydropyran-2-ol with (ethoxycarbonylethylidene) triphenylphospholane;

(2) protecting a free hydroxyl group of the reaction product from (1);

(3) transforming a hydroxymethyl group of the reaction product from (2) into a formyl group;

(4) reacting the reaction product from (3) with phosphonoacetic acid ester represented by the following general formula (A):

(A)

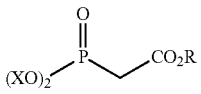

wherein R and X each represent a linear, branched, or cyclic alkyl or aryl group;

(5) reacting the reaction product from (4) with a base and acetaldehyde;

(6) formally dehydrating the reaction product from (5);

(7) deblocking a protecting group of the reaction product from (6);

(8) oxidizing the reaction product from (7);

(9) reacting the reaction product from (8) with phosphonopropionic acid methyl ester represented by the following general formula (B):

(B)

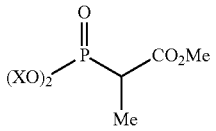

wherein X is defined as in (4) above;

(10) reacting the reaction product from (9) with acetonitrile in the presence of a base;

(11) reacting the reaction product from (10) with propanal represented by the following general formula (C):

(C)

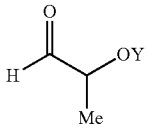

wherein Y represents a hydroxyl protecting group;

(12) epoxidizing the reaction product from (11);

(13) deblocking a protecting group of the reaction product from (12);

(14) dehydrating a cyano group from the reaction product from (13); and

(15) lactamizing the reaction product from (14).

3. A compound represented by the following general formula (III):

(III)

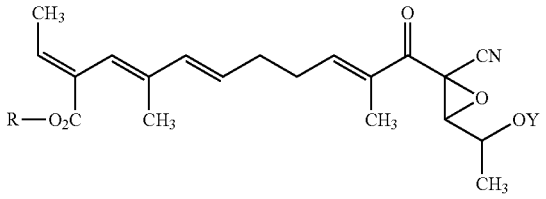

wherein R represents a methyl group, ethyl group, n-propyl group, isopropyl group, n-butyl group, isobutyl group, sec-butyl group, tert-butyl group, n-pentyl group, [or] n-hexyl group *or phenyl group* and Y represents a tert-butyldiphenylsilyl group, a tert-butyldimethylsilyl group, a triethylsilyl group, a *triisopropylsilyl* group, a dimethylethylsilyl group, a teterahydropyranyl group, an ethoxyethyl group, a methoxymethyl group or a benzyl group.

4. A process for producing a compound represented by the following general formula (III):

(III)

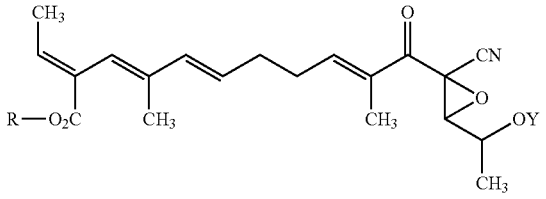

wherein R represents a linear, branched, or cyclic alkyl or aryl group and Y represents a hydroxyl protecting group, comprising reacting a compound represented by the following general formula (IV):

(IV)

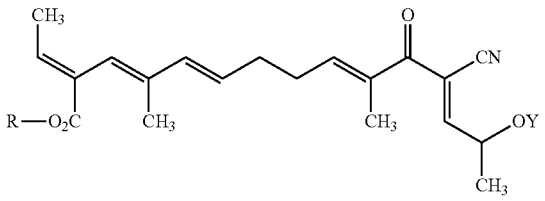

wherein R and Y are defined as above for (III), with a peroxide that [steroselectively] *stereoselectively* epoxidizes the compound (IV).

5. A pharmaceutical composition containing the compound according to claim 1 as an active ingredient and a pharmaceutically acceptable carrier.

6. The process according to claim 2, wherein R in the general formula (I) is a linear, branched, or cyclic alkyl group having 2 or more carbon atoms.

7. The process according to claim 2, wherein R in the general formula (I) is a linear, branched or cyclic alkyl group having 2 to 6 carbon atoms.

8. The process according to claim 2, wherein R in the general formula (I) is a tert-butyl group.

* * * * *